(12) United States Patent
Indermuhle

(10) Patent No.: US 8,765,077 B2
(45) Date of Patent: Jul. 1, 2014

(54) REAGENT DISPENSERS AND STACKABLE BARS FOR MULTIPLEX BINDING ASSAYS

(76) Inventor: Pierre F. Indermuhle, Berkeley, CA (US)

( * ) Notice: Subject to any disclaimer, the term of this patent is extended or adjusted under 35 U.S.C. 154(b) by 218 days.

(21) Appl. No.: 13/195,918

(22) Filed: Aug. 2, 2011

(65) Prior Publication Data
US 2012/0028844 A1 Feb. 2, 2012

Related U.S. Application Data

(60) Provisional application No. 61/370,076, filed on Aug. 2, 2010.

(51) Int. Cl.
*B01L 3/00* (2006.01)

(52) U.S. Cl.
USPC ........... 422/503; 422/400; 422/401; 422/407; 422/500; 422/501; 422/502; 422/504; 422/507; 422/521; 422/551; 422/553; 422/560; 422/561; 435/3; 435/285.1; 435/286.1; 435/286.2; 435/288.1; 435/288.4; 435/288.7; 435/303.1; 435/34; 435/374; 435/809; 435/6.1; 435/4; 435/7.1; 435/91.2; 436/157

(58) Field of Classification Search
USPC ......... 422/400, 401, 407, 500, 551, 553, 560, 422/561, 501, 502, 503, 504, 507, 521; 435/3, 285.1, 286.1, 286.2, 287.2, 435/288.1, 288.4, 288.7, 303.1, 34, 374, 6, 435/6.14, 7.1, 91.2, 809; 436/157
See application file for complete search history.

(56) References Cited

U.S. PATENT DOCUMENTS

2003/0008412 A1* 1/2003 Coffman et al. ............. 436/180

* cited by examiner

Primary Examiner — Dennis M White

(57) ABSTRACT

Multiplex binding assay assemblies are disclosed. The assemblies generally include at least one assay bar that includes a top side, a bottom side, and at least one well accessible from the top side of the assay bar. Each well includes a side surface, a bottom surface, an open top end, and at least one secondary container, with each secondary container including a capillary tube that (i) begins at a location within an interior volume of the well and (ii) ends at a location beneath the bottom surface of the assay bar. The assemblies further include a dispenser bar that is adapted to be positioned adjacent to the top side of the assay bar, which includes one or more reservoirs that are configured to provide one or more reagents to the at least one secondary container located in each well of the assay bar.

19 Claims, 5 Drawing Sheets

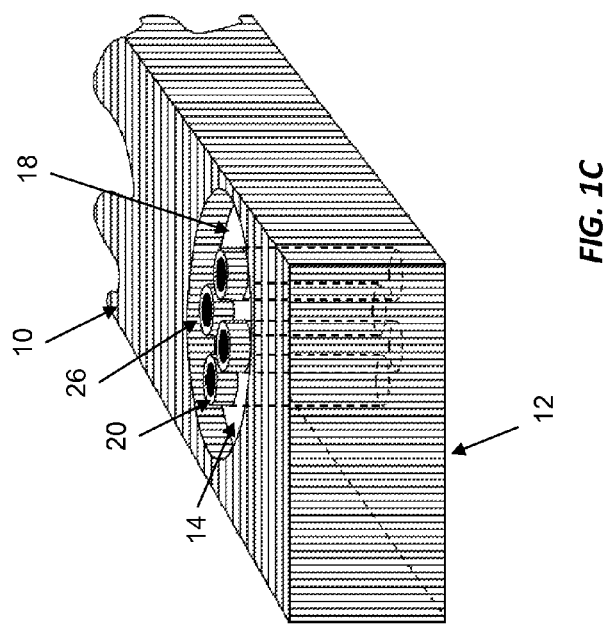
FIG. 1C
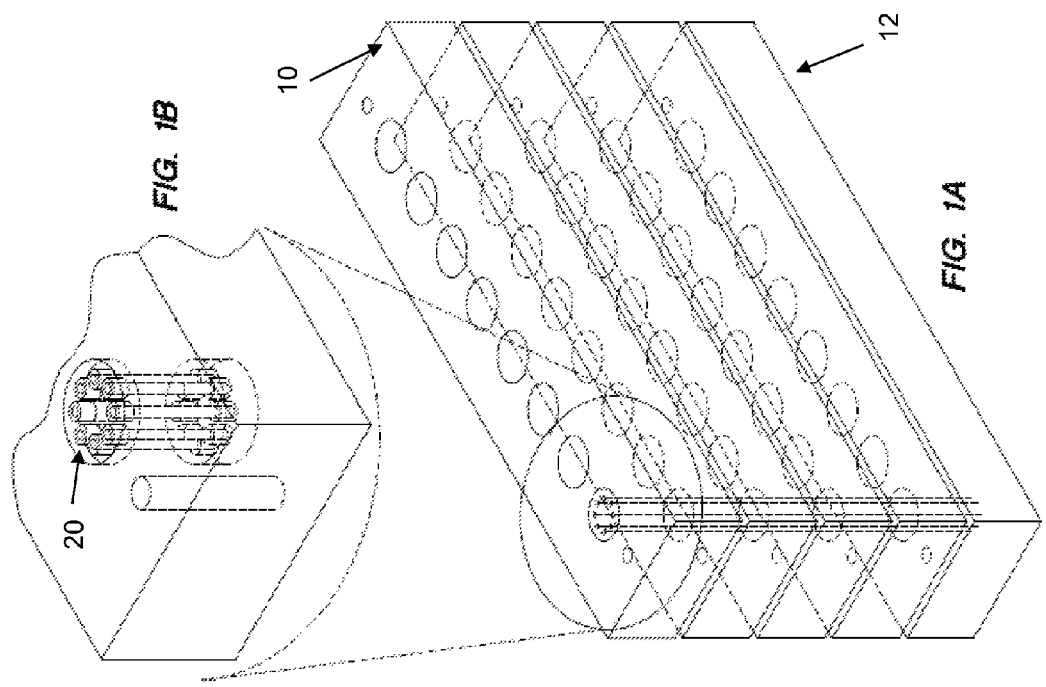
FIG. 1B
FIG. 1A

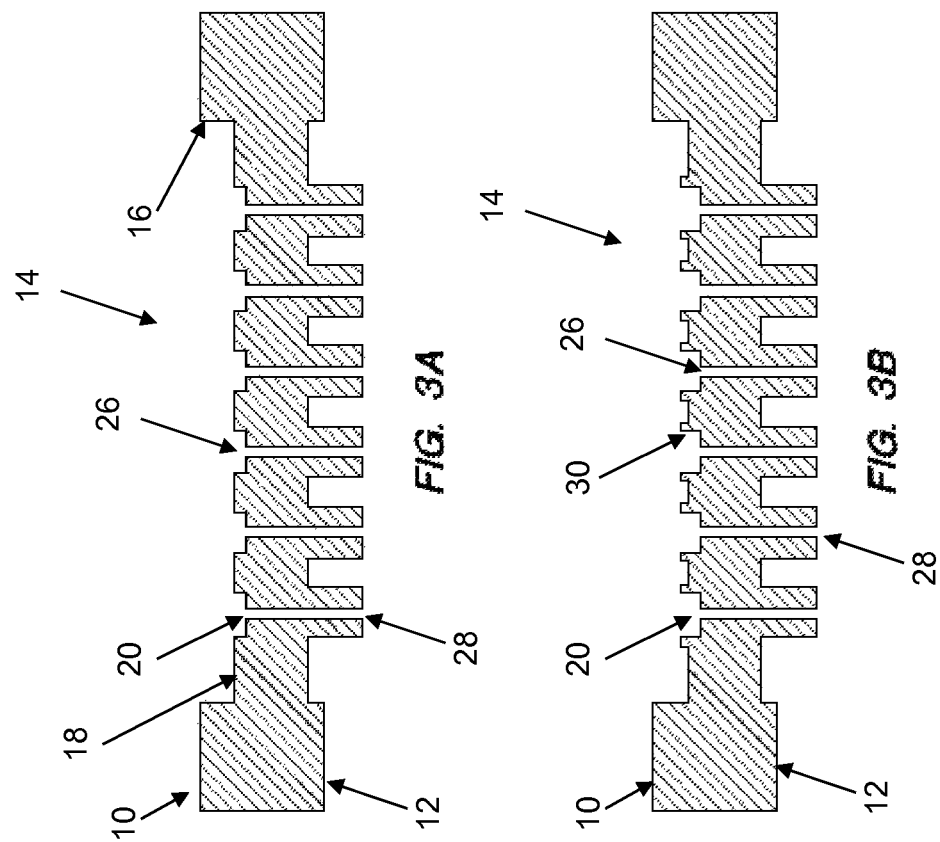

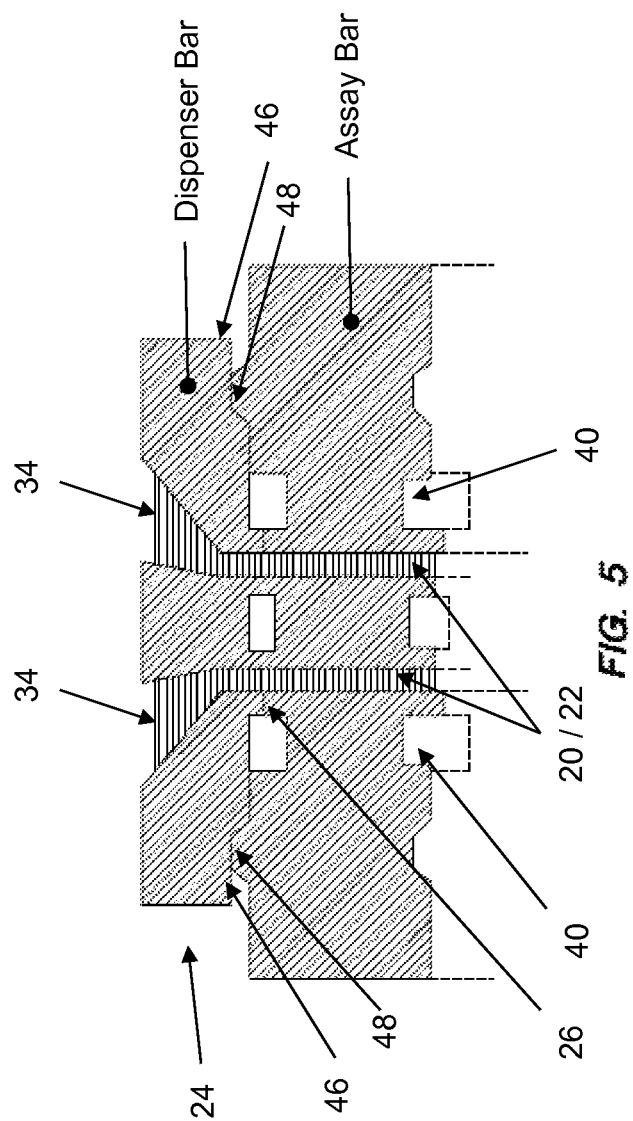

REAGENT DISPENSERS AND STACKABLE BARS FOR MULTIPLEX BINDING ASSAYS

CROSS-REFERENCE TO RELATED APPLICATIONS

This application claims priority to, and incorporates by reference, U.S. provisional patent application Ser. No. 61/370,076, which was filed on Aug. 2, 2010.

FIELD OF THE INVENTION

The field of the present invention relates to assemblies for use in multiplex binding assays. More particularly, the field of the present invention relates to reagent dispensers and stackable bars, which may be used to carryout multiplex binding assays.

BACKGROUND OF THE INVENTION

A multiplex assay is a type of procedure that simultaneously—in a single assay—measures, detects and/or analyzes multiple analytes. Multiplex assays have been used in order to detect or quantify various biomolecules in a particular sample, such as mRNAs, proteins, antibodies, and other biomolecules. Multiplex assay formats are often beneficial, insofar as such formats can provide a significant reduction in assay costs, on a cost-per-analyte basis. In addition, such formats significantly increase the amount (and often types) of information that can be extracted from each sample, particularly on a per-sample-volume basis.

Despite the significant utility of multiplex assay formats, present platforms do not allow for the dispensing of a specific secondary binding agent (i.e., the detection agent) to each of a plurality of immobilized targets, in order to reduce cross-reactivity (which leads to false positive results). This drastically limits the types of assays that may be combined in a multiplex fashion (and, more particularly, the combination of analytes that may be measured or detected in a single assay format). In addition, current platforms do not allow individual assay conditions, e.g., sample dilutions, buffer types, incubation times, etc., to be optimized. Accordingly, a continuing need exists for new and improved multiplex binding assay assemblies and methods of use thereof.

SUMMARY OF THE INVENTION

According to certain aspects of the present invention, multiplex binding assay assemblies are provided. The assemblies generally include at least one assay bar that includes a top side, a bottom side, and at least one well accessible from the top side of the assay bar. Each well includes a side surface, a bottom surface, an open top end, and at least one secondary container, with each secondary container including a capillary tube that (i) begins at a location within an interior volume of the well and (ii) ends at a location beneath the bottom side of the assay bar. The assemblies further include a dispenser bar that is adapted to be positioned adjacent to the top side of the assay bar, which includes one or more reservoirs that are configured to provide one or more reagents to the at least one secondary container located in each well of the assay bar.

According to certain related aspects of the present invention, multiplex binding assay assemblies are provided, which include a plurality of the identically-configured assay bars described herein stacked upon each other. Such assemblies further include a dispenser bar that is adapted to be positioned adjacent to the top side of a first assay bar included within the plurality of assay bars, when the assay bars are stacked upon each other. According to such embodiments, the first assay bar is positioned at the top of the stack, such that the dispenser bar may be stacked on top of the first assay bar. As explained above, the dispenser bar will comprise multiple reservoirs, each of which are configured to provide one or more reagents to a single secondary container located in a well of the first assay bar.

As described further below, each secondary container comprises a capillary tube that exhibits a length that is approximately equal to a distance between the top side and the bottom side of the assay bar. In certain embodiments, the top end of each secondary container may be recessed (within the wells) relative to the top side of the assay bar, with a bottom end of each secondary container extending below a plane that runs tangential with the bottom side of the assay bar. The invention provides that the arrangement of the plurality of secondary containers is preferably identical among all of the wells contained in all of the plurality of assay bars. Still further, the invention provides that upon stacking the plurality of assay bars upon each other, the secondary containers of the first assay bar are in fluid communication with the secondary containers of a second assay bar stacked directly beneath the first assay bar (and all other assay bars stacked directly beneath the second assay bar). According to such embodiments, the invention provides that a bottom end and top end of each secondary container of the assay bars are open, such that liquid may travel from each secondary container of a first assay bar to an adjacent secondary container of a second assay bar. The invention provides that the liquid will be retained within the secondary containers of the assay bars due to capillary forces.

According to additional aspects of the present invention, methods of using the assay bars (and assay bar assemblies) for carrying out multiplex binding assays are encompassed by the present invention.

The above-mentioned and additional features of the present invention are further illustrated in the Detailed Description contained herein.

BRIEF DESCRIPTION OF THE FIGURES

FIG. 1A: is a diagram of five stacked assay bars described herein, which comprise multiple groupings of capillaries (i.e., secondary containers), with each grouping being surrounded by a recess (i.e., a well).

FIG. 1B: is a diagram of a single recess (well) of an assay bar of FIG. 1A, which includes eight separate secondary containers.

FIG. 1C: is another diagram of a single recess (well) of an assay bar of the present invention, which includes four separate secondary containers.

FIG. 3A: is a cross-sectional diagram of an assay bar of the present invention in which the top ends of the secondary containers are recessed relative to the top surface of the assay bar (with the secondary containers protruding through the bottom surface of the surrounding well).

FIG. 3B: is a cross-sectional diagram of an assay bar of the present invention in which the top ends of the secondary containers are recessed relative to the top surface of the assay bar, and each secondary container further includes a protruding edge (at the top end thereof).

FIG. 5 is a side, cross-sectional view of an assay bar of the present invention, with a dispenser bar positioned on the top side thereof.

DETAILED DESCRIPTION OF THE INVENTION

Figure 2:
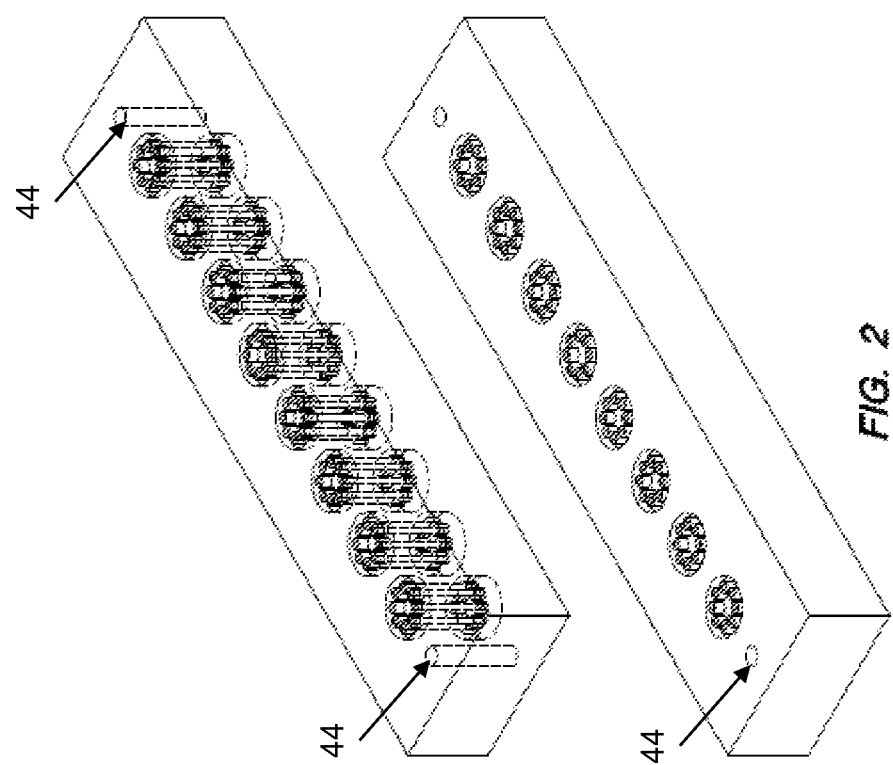
FIG. 2: is another diagram of a non-limiting example of the assay bars described herein, which comprise eight separate wells, with each well including a grouping of eight secondary containers.

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

Referring now to FIGS. 1-5, the invention provides assay bars and reagent dispensers that may be used to carry out multiplex binding assays. The assay bars generally include a top side 10, a bottom side 12, and at least one secondary container 20 accessible from the top side 10 of the assay bars. In certain embodiments, the assay bars further include at least one well 14 accessible from the top side 10 of the assay bars. According to such embodiments, each well 14 includes a side surface 16 and a bottom surface 18, with the at least one secondary container 20 protruding through the bottom surface 18 of each well 14 (and being accessible from the top side 10 of the assay bar). In certain preferred embodiments, a plurality of secondary containers 20 will protrude through the bottom surface 18 of each well 14 (and be accessible from the top side 10 of the assay bar).

A dispenser bar 24 (FIG. 5) is also encompassed by and used in connection with the present invention. The dispenser bar 24 is configured and adapted to be positioned adjacent to the top side 10 of the assay bars (FIG. 5). The dispenser bar 24 is configured to provide one or more reagents to the one or more secondary containers 20 of an assay bar.

According to certain preferred embodiments, the secondary containers 20 consist of a capillary tube 22, which may span a distance (length) that is equal to the thickness (or approximately equal to the thickness) of the assay bar, with the "thickness" of the assay bar being the distance between the top side 10 and bottom side 12 thereof. The invention provides that the location and arrangement of the secondary containers 20 in each well 14 will preferably be identical among the assay bars, such that the secondary containers 20 of multiple assay bars are aligned and directly adjacent to each other when the assay bars are stacked upon each other, as illustrated in FIGS. 1A and 2.

That is, when the assay bars are stacked upon each other in an aligned manner, the bottom end 28 (FIG. 3) of each secondary container 20 of a first assay bar is aligned with the top end 26 of a corresponding secondary container 20 of the underlying assay bar. This provides for fluid communication between the secondary containers 20 of stacked assay bars, such that a dispenser bar 24 may be used to deliver reagents to the secondary containers 20 of multiple assay bars (when such assay bars are stacked upon each other).

According to certain embodiments of the invention, the secondary containers 20 may begin at a top end 26 that is located at (or near) a plane that runs tangential to the top side 10 of the assay bar. According to such embodiments, the bottom ends 28 of the secondary containers 20 will preferably be located at (or near) a plane that runs tangential with the bottom side 12 of the assay bar. As such, the top ends 26 and bottom ends 28 of the secondary containers 20 will span the entire width or thickness of the assay bar. As explained above, this configuration allows the secondary containers 20 of a first assay bar to be located directly adjacent to, and in fluid communication with, the secondary containers 20 of a second assay bar, when such assay bars are stacked upon each other. The invention provides that the bottom side 12 of the assay bar may, optionally, comprise a recess 40 around each secondary container 20.

According to certain additional embodiments of the invention, the secondary containers 20 may begin at a top end 26 that protrudes through the bottom surface 18 of a well 14 (or recessed area 14), and into an interior volume thereof, but ends prior to reaching a plane that runs tangential to the top side 10 of the assay bar. That is, the top ends 26 of the secondary containers 20 may be recessed relative to the top side 10 of the assay bar. According to such embodiments, the bottom ends 28 of the same secondary containers 20 may extend beyond a plane that runs tangential with the bottom side 12 of the assay bar. Preferably, according to such embodiments, the bottom ends 28 of the secondary containers 20 will extend beyond such bottom side 12 by a distance $\Delta_1$, wherein the distance of $\Delta_1$ represents the distance between the top end 26 of each secondary container 20 and the top side 10 of the assay bar.

This way, as explained above relative to other embodiments of the present invention, multiple assay bars may be stacked upon each other, with the secondary containers 20 of the stacked assay bars being directly adjacent to and in fluid communication with each other. That is, when the bottom ends 28 of the secondary containers 20 extend beyond the bottom side 12 of the assay bar by a distance $\Delta_1$, such bottom ends 28 will be of sufficient length to be located directly adjacent to the recessed top ends 26 of the secondary containers 20 in the assay bar located (stacked) directly beneath it. As explained above, relative to other embodiments, this provides for fluid communication between the secondary containers 20 of stacked assay bars, such that a dispenser bar 24 may be used to simultaneously deliver reagents to the secondary containers 20 of multiple assay bars (when such assay bars are stacked upon each other).

The invention provides that (in addition to being stacked upon each other) the assay bars may be positioned side-by-side. According to such embodiments, if the assay bars exhibit a number of wells 14 that are the same as those found in a row or column of a standard assay plate (e.g., a 96-well or 384-well assay plate), a series of the assay bars may be located adjacent to each other to achieve the configuration of a standard assay plate. For example, some assay plates comprise a total of 96 wells, configured with 12 columns and 8 rows of wells. If a series of assay bars comprise 8 wells 14, a series of 12 of such assay bars may be located adjacent to each other, such that the assay bars would collectively exhibit approximately the same dimensions (and number of wells 14) as a standard 96-well assay plate. In another example, if a series of assay bars comprise 12 wells 14, a series of 8 of such assay bars may be located adjacent to each other, such that the assay bars would collectively exhibit approximately the same dimensions (and number of wells 14) as a standard 96-well assay plate.

The well 14 (or recessed area 14) may be used as a reservoir to deliver a reagent (or sample) to the one or more secondary containers 20 located within such well 14. More particularly, when the top ends 26 of the secondary containers 20 are recessed relative to the top side 10 of the assay bar, a reagent (or sample) may be dispensed into the well 14. If such reagent (or sample) is dispensed into the well 14 to a volume that causes such reagent to exceed the extent to which the secondary containers 20 protrude into the interior of such well 14, the reagent (or sample) will flow into the secondary containers 20 located therein. As such, the well 14 may also be used as a reservoir to deliver a reagent (or sample) to the one or more secondary containers 20 located within such well 14.

Referring to FIG. 3B, the invention provides that the recessed top ends 26 of the secondary containers 20 may comprise a protruding edge 30, which is effective to facilitate control and retention of reagent (or sample) inside the secondary containers 20. Additionally, the invention provides that such protruding edge 30 may comprise one or more notches (located on the top surface of the protruding edges 30), which will facilitate the transfer of liquid into the interior of the secondary containers 20. Still further, the invention provides that the top ends 26 and/or bottom ends 28 of the secondary containers 20 may be configured to improve and facilitate the transfer of reagent from one secondary container 20 (of a first assay bar) to another secondary container 20 (of a second assay bar). For example, the ends of the secondary containers 20 may be beveled, indented, or exhibit other configurations that would facilitate the transfer of reagent from one secondary container 20 to another.

The invention provides that when the secondary containers 20 are cylindrical, the secondary containers 20 will exhibit a diameter of about 1 millimeter (or less) or, alternatively, may exhibit a diameter of 500 micrometers, 200 micrometers, or 100 micrometers (or other diameters within such ranges). When the secondary containers 20 are configured in such manner, surface tension forces dominate liquid behavior, and will cause reagents loaded into the secondary containers 20 to be pulled into and contained within the secondary containers 20. A capillary barrier will retain the reagent within the secondary containers 20, until otherwise drawn therefrom by force (e.g., during a reagent decanting step) or by making contact with another secondary container 20 of another assay bar, e.g., when multiple assay bars are stacked upon each other.

The invention provides that reagent will not leak from the secondary containers 20 as a result of these capillary forces (capillary barriers). As such, once the secondary containers 20 of multiple stacked assay bars have been filled with reagent, the assay bars may be separated from each other for further processing, and the reagent will remain in such secondary containers 20 vis-à-vis capillary forces (capillary barriers). If the reagent contains magnetic micro-beads, magnets may be used to prevent the beads from falling out of the secondary containers 20, e.g., during decanting and rinsing steps. That is, the assay bars may comprise a magnetic bar that may be reversibly affixed to the assay bar, which is positioned in sufficient proximity to the secondary containers 20 to magnetically retain any magnetic micro-beads that may be contained within a reagent, inside the secondary containers 20.

According to certain preferred embodiments of the present invention, the assay bars of the present invention may comprise a plurality of wells 14—each of which may have one or more secondary containers 20 and, preferably, will comprise multiple secondary containers 20. For example, the assay bars of the present invention may exhibit a length (or width) that is equal to, or approximately equal to, the length of a standard 96-well plate. According to such example, the assay bar may comprise 8, 12, 16, or 24 groups of secondary containers 20, with each group of secondary containers 20 optionally being contained within its own well 14, as illustrated, for example, in FIG. 2. According to such embodiments, each group of secondary containers 20 may comprise from 2-20 secondary containers 20. The thickness of the assay bars may range between, for example, 10-15 millimeters, with the length of the secondary containers 20 preferably being consistent with such thickness—i.e., from 10-15 millimeters. However, in certain alternative embodiments, the length of the secondary containers 20 may be less than the thickness of the assay bar, e.g., the secondary containers 20 may exhibit a length that ranges from 5-10 millimeters.

As described above, the invention provides that the secondary containers 20 included in the wells 14 may be open at both ends, i.e., at the opening within the well 14 (at the top end of each secondary container 20) and at an opening located at (or below) the bottom side 12 of the assay bar (at the bottom end 28 of each secondary container 20). According to yet further embodiments of the present invention, however, the secondary containers 20 may comprise a restriction located at (or near) the bottom ends of the secondary containers 20. The restriction will preferably be effective to retain liquid inside of the secondary containers 20 through capillary forces. This restriction may be integrally formed with the secondary containers 20. Alternatively, the restrictions may be applied, when needed, to the bottom ends 28 of the secondary containers 20 during the performance of an assay.

According to such embodiments, the "restriction" may comprise, by way of example and not limitation, a narrowing of the bottom end 28 of the secondary container 20 (to reduce the size/diameter of the aperture at the bottom end 28 thereof to encourage a capillary barrier). Alternatively, the restriction may comprise a circular disc, which includes an aperture smaller than the aperture (internal diameter) of the secondary container 20, which may be applied to the bottom end 28 of the secondary container 20. Such a disc may be made out of hydrophobic material or be coated with a hydrophobic layer. Still further, the restriction may consist of a grid, with a mesh size smaller than the aperture of the secondary container 20, which may be applied to the bottom end 28 of the secondary container 20. This geometry is advantageous insofar as it only requires a relatively low precision alignment, relative to the end of the secondary container 20. Such a grid may be comprised of hydrophobic material or be coated with a hydrophobic layer.

In addition, the restriction may comprise a porous membrane that may be applied to the bottom end 28 of the secondary container 20. According to yet further non-limiting examples, the restriction may comprise a restriction bar, which includes an array of features that may be applied to the bottom ends 28 of all secondary containers 20 included within an assay bar. The dimensions of this restriction bar will preferably match the dimensions of the assay bar, with the secondary containers 20 positioned such that both bars may be aligned respective to each other—with the flow restrictive features being applied to the bottom ends 28 of all secondary containers 20. The restrictive features may protrude from the surface of the restriction bar, so that they may be easily positioned in a manner that is adjacent to the bottom ends 28 of the secondary containers 20.

Figure 4A:
FIG. 4A: is a side transparent view of an assay bar of the present invention.
Figure 4B:
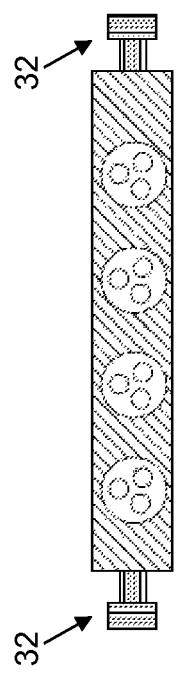
FIG. 4B: is a top side view of the assay bar of FIG. 4A.
Figure 4C:
FIG. 4C: is a side view of the assay bar of FIG. 4A.

Referring to FIG. 4, the sides of the assay bars may include an alignment feature 32, which may be inserted into a set of parallel guiding rails of an alignment jig (not shown), which allows the bars to be moved from a stacked configuration to a plate (side-by-side) configuration. For example, an alignment jig may comprise at least two elongated and linear rails, with each liner rail comprising a groove. The linear rails (and grooves) run parallel to each other, with a first groove receiving a protruding element 32 of a first side of the assay bars, and a second groove receiving a protruding element 32 of a second side of the assay bars (FIG. 4). According to such embodiments, the assay bars may be maintained in order within such alignment jig, and even converted from a stacked configuration to a side-by-side configuration, as desired.

Still further, the assay bars of the present invention may comprise a means for aligning a set of assay bars on top of each other. For example, referring to FIG. 2, each assay bar may comprise a set of apertures 44, located on the top side 10 of the assay bar. The apertures 44 may be configured to receive a set of tabs (or protruding elements), which extend from the bottom side 12 of an assay bar that is stacked on the top of such assay bar. That is, the assay bars may comprise the set of apertures 44 located on the top side 10 thereof, and a set of corresponding tabs (or protruding elements) located on the bottom side 12 thereof, such that a set of assay bars may be stacked upon each other and properly aligned when the tabs (or protruding elements) located on the bottom side 12 of an assay bar are inserted into the apertures 44 located on the top side 10 of an assay bar stacked directly beneath it.

As mentioned above, a dispenser bar 24 is also encompassed by and used in connection with the present invention. The dispenser bar 24 is configured and adapted to be positioned (and mounted) adjacent to the top side 10 of the assay bars (FIG. 5). The dispenser bar 24 is configured to provide one or more reagents to the one or more secondary containers 20 of an assay bar.

Still referring to FIG. 5, the invention provides that the dispenser bar 24 comprises at least one reservoir 34 (and preferably multiple reservoirs 34), which is in fluid communication with the top end 26 of the secondary container 20 (e.g., the portion that protrudes through the bottom surface 18 of the well 14 and into an interior volume thereof), when the dispenser bar 24 is positioned adjacent to the top side 10 of the assay bar. Preferably, the reservoir(s) 34 will exhibit a larger diameter (or cross-section when viewed from above), relative to the diameter (or cross-section) of the secondary containers 20, such that reagents may be easily and manually added to such reservoir(s) 34—e.g., using a micropipette or other similar device.

The invention provides that the same reagent may be provided to each reservoir 34 of the dispenser bar 24 or, alternatively, different reagents may be provided to such reservoirs 34. This way, if desirable, the same well 14 may be provided with multiple types of reagents, with different reagents being provided to the different secondary containers 20 of a particular well 14 via the separate reservoirs 34 of the dispenser bar 24.

The invention provides that the reservoirs 34 of a dispenser bar 24 may be filled with a reagent, such that the dispenser bar 24 may then be aligned with and placed over an assay bar (or set of stacked assay bars), in order to then fill the secondary containers 20 of such assay bars as described herein. Alternatively, the dispenser bar 24 may first be aligned with and placed over an assay bar (or set of stacked assay bars), and then filled with a reagent, which will then travel from the dispenser bar 24 and into the secondary containers 20 of the assay bars. As described above, invention provides that the dispenser bar 24 may comprise aligning elements, which may be used to properly align and position the dispenser bar 24 on top of an assay bar.

The invention provides that desired reagents or other liquids will travel from the reservoirs 34 of the dispenser 24 and into the secondary containers 20 of an assay bar by way of capillary forces. The invention provides that the protruding edges 30 at the top ends 26 of the secondary containers 20 may be inserted into the separate reservoirs 34 of the dispenser bar 24. For example, upon inserting the protruding edges 30 of a secondary container 20 into a separate reservoir 34 of the dispenser bar 24 that is filled with a reagent, the reagent will travel from the reservoir 34 (and be pulled) into the secondary container 20 by capillary action (and into the secondary containers 20 of assay bars on which a first assay bar is stacked).

Alternatively, as illustrated in FIG. 5, the invention provides that placing the secondary containers 20 of an assay bar directly adjacent to the reservoirs 34 of the dispenser bar 24 will also cause reagent to travel from the dispenser bar 24 and into the secondary containers 20 by capillary action (without necessarily inserting the protruding edges 30 of the secondary containers 20 into the separate reservoirs 34 as described above). The reagent will stop flowing when the dispenser bar 24 is removed from the assay bar(s), or when the secondary containers 20 become full, due to the capillary barrier that will form at the bottom ends 28 of the secondary containers 20.

The invention may employ the use of certain mechanical means for ensuring that the dispenser 24 is properly aligned and positioned adjacent to the top side 10 of an assay bar. For example, the bottom side of the dispenser 24 may include an area 46 (e.g., a notch) that is configured to receive a correspondingly-configured protruding element 48 located on the top side 10 of the assay bars, such that when the protruding elements 48 are inserted into such areas 46 (e.g., a notches), the dispenser 24 is properly aligned and positioned adjacent to the top side 10 of the assay bar.

The invention provides that the volume of reagent (or other liquid) that the secondary containers 20 of an assay bar will hold may be determined based on the internal volume of the secondary containers 20. For example, in the case of cylindrically-configured secondary containers 20, the volume of such containers may be calculated using the following formula:

$$\text{Volume} = \pi \times r^2 \times h \, (\text{pi} \times \text{radius-squared} \times \text{height})$$

Although the secondary containers 20 are illustrated to be cylindrical (and to therefore have a circular cross-section) in FIGS. 1-5, the invention provides that the secondary containers 20 may exhibit other geometries.

According to certain additional and alternative embodiments of the invention, the secondary containers 20 of the assay bars may be provided with reagent through forces other than capillary action. For example, reagent may be dispensed into the secondary containers 20 through mere gravitational forces or, alternatively, a reagent may be dispensed therein using an external pressure source (from a pressurized dispenser or other source of reagent, such as single or multiple pipettes).

Both the dispenser bars 24 and the assay bars described herein may be fabricated at low cost using plastic injection molding. For example, the dispenser bars 24 and the assay bars may be comprised of polystyrene, polypropylene, polycarbonate, or other suitable materials. Still further, the invention provides that the dispenser bars 24 and the assay bars may consist of multiple materials. For example, a majority of a bar may be manufactured from one of the plastics listed above, whereas the secondary containers 20 (or just the internal surface areas thereof) may be comprised of metals, glass, or other materials, e.g., by inserting a separate sleeve or tubing into such secondary containers 20. The molds that are necessary to fabricate the dispenser bars 24 and the assay bars could be made by high-resolution machining, laser machining or micro-fabrication techniques to achieve the required precision.

The invention provides that the beginning of a multiplex binding assay may be carried out and set up using the assemblies described herein, by placing a dispenser bar 24 on the top side 10 of an assay bar (or set of stacked assay bars). As described herein, the dispenser bar 24 will comprise one or more reservoirs 34, which are in fluid communication with the top end 26 of the secondary containers 20 of such assay bar (or the assay bar located at the top of a stack of assay bars). This way, a desired reagent or other liquid may be loaded (filled) into a certain secondary container 20, or group of secondary containers 20, by dispensing an appropriate volume of such reagent or other liquid into the reservoir(s) 34 above the target secondary container(s) 20.

As mentioned above, the invention contemplates that different types of reagents or other liquids may be loaded into separate reservoirs 34 of the dispenser bar 24 and, therefore, into separate secondary containers 20 of an assay bar. Of course, the type of reagent(s) added to the secondary containers 20 (and well 14) of an assay bar will depend on the type of assay being performed. The invention does contemplate that, in addition to traditional reagents, such reagents may include micro-beads (including, without limitation, magnetic micro-beads).

As mentioned above, the invention provides that a multiplexing binding assay may begin by positioning a dispenser bar 24 on the top side 10 of an assay bar (or on the top side 10 of an assay bar of a stack of assay bars). Next, a reagent containing the desired receptors or antibodies (i.e., capture agents) are dispensed into the individual secondary containers 20 vis-à-vis the reservoirs 34 of the dispenser bar 24. Such receptors (capture agents) are then allowed to become bound to or immobilized on the interior surface of the secondary containers 20, or otherwise immobilized within the secondary containers 20 via magnetic or other forces, e.g., immobilizing the receptors (capture agents) that are bound to magnetic beads within the secondary containers 20 by placing (and optionally affixing) a magnetic element on the assay bar in sufficient proximity of the secondary containers 20 to retain such beads therein.

Next, such reagents are decanted out of the assay bar, while the immobilized receptors (capture agents) remain bound to the interior sides of the secondary containers 20 or otherwise retained therein via other forces. If multiple assay bars are employed, at this time, the various assay bars may be un-stacked and separated from each other—and, optionally, placed side-by-side into a configuration that is compatible with standard assay plates (e.g., 96- or 384-wells). The test samples may then be added to the secondary containers 20, e.g., by dispensing the samples into the wells 14, whereupon the test samples will enter the secondary containers 20 via capillary action and be allowed to interact with the immobilized receptors (capture agents) therein. The samples are then allowed to incubate for an appropriate period of time (and, if the above-referenced magnetic element is used, such element is removed from the assay bar during this incubation period).

According to such example, after the test samples are decanted from the assay bar, the secondary containers 20 may be rinsed with an appropriate buffer. Here again, if magnetic beads have been added to the secondary containers 20, the magnetic element should be returned and affixed to the assay bar during this rinsing step, in order to retain the beads inside the secondary containers 20. Following this rinsing step, if multiple assay bars are employed, the assay bars may be stacked upon each other as described herein.

A clean dispenser bar 24 is then placed on the top side 10 of the assay bar (or on the top side 10 of the assay bar located on a stack of assay bars). A specific secondary binding agent or antibody (i.e., the detection agent) may then be added to the secondary containers 20 of the assay bar(s) and allowed to incubate, in order to detect (and potentially quantify) agents, e.g., proteins, that were present in the sample and which bound to the immobilized receptors (capture agents). If magnetic beads are used, the magnetic element referenced above is removed from the assay bar(s) during this incubation period. The detection agent may be tethered to a molecule or agent, e.g., a fluorescent tag, which may be detected using standard instrumentation. Following the appropriate incubation period for the detection agent, the assay bars may be separated and individually analyzed using an appropriate device to quantitate the amount of detection agent that has bound to immobilized sample agent that bound to the immobilized receptors (capture agents). The specific detection device that is used will depend on the nature of the detection agent, e.g., a fluorometer will be used to detect and quantify detection agents with fluorescent tags. Alternatively, the invention provides that the assay bars may be placed side-by-side to achieve a standard assay plate configuration (e.g., 96-well or 384-well), and then simultaneously loaded into a detection instrument for analysis.

In addition to the assay bar assemblies described herein (i.e., the assay bars with the dispenser bars 24), the present invention further encompasses the assay bars described herein, without the dispenser bars 24. In addition, methods of using the assay bars (and assay bar assemblies) for carrying out multiplex binding assays are encompassed by the present invention. The multiplex assay assemblies (and methods of use thereof) allow for the multiplexing of small volume samples—and for the separate dispensing of the reagents required by each of the multiplex assays. This way, each assay can be optimized individually, which leads to better assay quality (both in terms of reproducibility and sensitivity), and renders the modification of an assay panel possible without requiring the re-optimization of the entire panel.

Although certain example methods, apparatus, and/or articles of manufacture have been described herein, the scope of coverage of this disclosure is not limited thereto. On the contrary, this disclosure covers all methods, apparatus, and/or articles of manufacture fairly falling within the scope of the appended claims—either literally or under the doctrine of equivalents.

What is claimed is:

1. A multiplex binding assay assembly, which comprises:
   (a) at least one assay bar that comprises a top side, a bottom side, and at least one well accessible from the top side of the assay bar, wherein each well comprises a side surface, a bottom surface, an open top end, and at least one cylindrical secondary container, wherein each cylindrical secondary container consists of a capillary tube that (i) begins at a location within an interior volume of the well, (ii) is surrounded by and protrudes through the bottom surface of each well, and (iii) ends at a location beneath the bottom side of the assay bar; and
   (b) a dispenser bar that is adapted to be positioned adjacent to the top side of the assay bar, which comprises one or more reservoirs that are configured to provide one or more reagents to the at least one secondary container located in each well of the assay bar.

2. The multiplex binding assay assembly of claim 1, which comprises a plurality of assay bars, which are identically configured and adapted to be stacked upon each other, wherein each well of each assay bar comprises multiple secondary containers that are arranged in an identical manner among each well of each of the assay bars.

3. The multiplex binding assay assembly of claim 2, wherein a plurality of secondary containers located in a first assay bar are in fluid communication with a plurality of secondary containers located in a second assay bar that is positioned and stacked directly beneath the first assay bar.

4. The multiplex binding assay assembly of claim 1, wherein each reservoir of the dispenser bar is in fluid communication with the at least one secondary container located in the assay bar, when the dispenser bar is positioned adjacent to the top side of the assay bar.

5. The multiplex binding assay assembly of claim 3, wherein each reservoir is in fluid communication with at least one secondary container located in a first assay bar that is stacked upon a plurality of additional assay bars, when the dispenser bar is positioned adjacent to the top side of the first assay bar.

6. The multiplex binding assay assembly of claim 1, wherein the at least one secondary container comprises a restriction at its bottom end, which is effective to assist in retaining the one or more reagents dispensed therein, wherein the restriction may be (a) integrally formed with the secondary container or (b) applied to the bottom end of the secondary container during use of the assay bar.

7. The multiplex binding assay assembly of claim 1, wherein the at least one secondary container is adapted to receive the one or more reagents when the reagents are dispensed therein via gravity or through an external pressure source.

8. A multiplex binding assay assembly, which comprises:
(a) a plurality of assay bars that each comprise a top side, a bottom side, and a plurality of wells accessible from the top side of each assay bar, wherein each well comprises a side surface, a bottom surface, an open top end, and a plurality of cylindrical secondary containers, wherein each cylindrical secondary container consists of a capillary tube that (i) begins at a location within an interior volume of the well, (ii) is surrounded by and protrudes through the bottom surface of each well, and (iii) ends at a location beneath the bottom side of the assay bar; and
(b) a dispenser bar that is adapted to be positioned adjacent to the top side of a first assay bar included within the plurality of assay bars, when said assay bars are stacked upon each other and said first assay bar is positioned at a top of said stack, wherein the dispenser bar comprises multiple reservoirs, each of which are configured to provide one or more reagents to a single secondary container located in a well of the first assay bar.

9. The multiplex binding assay assembly of claim 8, wherein each secondary container comprises a capillary tube that exhibits a length that is approximately equal to a distance between the top side and the bottom side of the assay bar.

10. The multiplex binding assay assembly of claim 9, wherein a top end of each secondary container is recessed relative to the top side of the assay bar.

11. The multiplex binding assay assembly of claim 10, wherein a bottom end of each secondary container extends below a plane that runs tangential with the bottom side of the assay bar.

12. The multiplex binding assay assembly of claim 11, wherein the bottom end of each secondary container extends below the plane that runs tangential with the bottom side of the assay bar by a distance of $\Delta_1$, wherein the distance of $\Delta_1$ equals the distance between the top end of each secondary container and the top side of the assay bar.

13. The multiplex binding assay assembly of claim 12, wherein the arrangement of the plurality of secondary containers is identical among all of the wells contained in all of the plurality of assay bars.

14. The multiplex binding assay assembly of claim 9, wherein upon stacking the plurality of assay bars upon each other, the secondary containers of the first assay bar are in fluid communication with the secondary containers of a second assay bar stacked directly beneath the first assay bar.

15. The multiplex binding assay assembly of claim 14, wherein a bottom end of each secondary container of the first assay bar is open, wherein a top end of each secondary container of the second assay bar is open, such that liquid may travel from each secondary container of the first assay bar to an adjacent secondary container of the second assay bar.

16. The multiplex binding assay assembly of claim 15, wherein the liquid is retained within the secondary containers of the assay bars due to capillary forces.

17. The multiplex binding assay assembly of claim 14, wherein upon stacking the plurality of assay bars upon each other, the secondary containers of the first assay bar are in fluid communication with the secondary containers of the second assay bar stacked directly beneath the first assay bar, and the secondary containers of the first assay bar and second assay bar are in fluid communication with the secondary containers of all other assay bars included within the plurality of assay bars.

18. The multiplex binding assay assembly of claim 17, wherein the plurality of assay bars may be separated and placed side-by-side, whereupon the plurality of assay bars, as a unit, exhibits a total number of wells that is the same as a number of wells included in a standard assay plate.

19. The multiplex binding assay assembly of claim 18, wherein the standard assay plate includes 96 wells or 384 wells.

* * * * *